(12) United States Patent
Seitz et al.

(10) Patent No.: US 7,115,603 B2
(45) Date of Patent: *Oct. 3, 2006

(54) Δ¹-PYRROLINES

(75) Inventors: Thomas Seitz, Langenfeld (DE); Martin Füsslein, Düsseldorf (DE); Johannes-Rudolf Jansen, Monheim (DE); Udo Kraatz, Leverkusen (DE); Christoph Erdelen, deceased, late of Leichlingen (DE); by Angelika Lubos-Erdelen, legal representative, Leichlingen (DE); Andreas Turberg, Haan (DE); Olaf Hansen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 162 days.

This patent is subject to a terminal disclaimer.

(21) Appl. No.: 10/494,204

(22) PCT Filed: Nov. 4, 2002

(86) PCT No.: PCT/EP02/12259

§ 371 (c)(1),
(2), (4) Date: May 3, 2004

(87) PCT Pub. No.: WO03/040130

PCT Pub. Date: May 15, 2003

(65) Prior Publication Data

US 2005/0228028 A1 Oct. 13, 2005

(30) Foreign Application Priority Data

Nov. 7, 2001 (DE) ................ 101 54 515

(51) Int. Cl.
C07D 401/10 (2006.01)
(52) U.S. Cl. ................... 514/243; 546/276.4
(58) Field of Classification Search ........... 514/243; 546/276.4
See application file for complete search history.

(56) References Cited

U.S. PATENT DOCUMENTS

| 6,274,613 B1 | 8/2001 | Plant et al. | 514/408 |
| 6,489,490 B1 | 12/2002 | Plant et al. | 548/525 |
| 6,599,924 B1 | 7/2003 | Plant et al. | 514/343 |
| 6,632,833 B1 | 10/2003 | Plant et al. | 514/422 |

FOREIGN PATENT DOCUMENTS

| WO | 94/29268 | 12/1994 |
| WO | 02/46151 | 6/2002 |

OTHER PUBLICATIONS

Tetrahedron Lett. 38, No. 22, (month unavailable) 1997, pp. 3841-3844, André Giroux et al "One Pot Biaryl Synthesis via in situ Boronate Formation".

Aust J. Chem., 17, (month unavailable) 1964, pp. 794-802, D.J. Brown et al, "Pyrimidine Reactions".

Chem. Ber. 125, (month unavailable) 1992, pp. 1169-1190, Carsten Bolm et al, "Enantioselective Synthesis of Optically Active Pyridine Derivatives and $C_2$-Symmetric 2,2'-Bipyridines".

Chem. Pharm. Bull., 43(2), Feb. 1995, pp. 247-255, Toshimi Seki et al, "Studies on Agents With Vasodilator and β-Blocking Activities. ll".

Eur. J. Med. Chem., 24, (month unavailable) 1989, pp. 249-257, Robert J. Ife et al, "Non-basic histamine $H_1$-antagonists. I. Synthesis and biological evaluation of some substituted 2-(2-pyridylaminoalkylamino) pyrimidones and related compounds".

J. Chem. Soc. (C), (month unavailable) 1971, pp. 1889-1891, B.W. Arantz et al, "Pyrimidine Reactions. Part XXII. The Relative Reactivities of Some Corresponding Chloro-, Bromo-, and Iodo-pyrimidines in Aminolysis".

J. Chem. Soc. Perkin Trans. 1 (month unavailable) 1995, pp. 2497-2502, Kiyoshi Matsumoto et al, Ag+ Ion-selective lariat ethers: high pressure syntheses and cation recognition properties.

J. Med. Chem., 34, (month unavailable) 1991, pp. 315-319, Werner Tjarks et al, "Boron-Containing Thiouracil Derivatives for Neutron-Capture Therapy of Melanoma".

J. Org. Chem., 49, (month unavailable) 1984, pp. 2240-2245, Dale L. Boger et al, "Intramolecular Diels-Alder Reactions of 1,2-Diazines: General Indoline Synthesis. Studies on the Preparation of the Central and Right-Hand Segments of CC-1065".

J. Org. Chem., 55, (month unavailable) 1990, pp. 69-73, Daniel L. Comins et al, "Lithiation of Methoxypyridines Directed by α-Amino Alkoxides".

Org. Prep. Proced. Int., 30(4), (month unavailable) 1998, pp. 433-437, Hanna Wojtowica-Rajchel et al, "Facile Synthesis of 5-(Dihydroxyboryl)-2,4-*bis*(Alkoxy)Pyrimidines and N(1)-Substituted 5-(Dihydroxyboryl)Uracils".

(Continued)

*Primary Examiner*—Kamal A. Saeed
(74) *Attorney, Agent, or Firm*—Richard E.L. Henderson

(57) ABSTRACT

This invention relates to novel Δ¹-pyrrolines of formula(I)

(I)

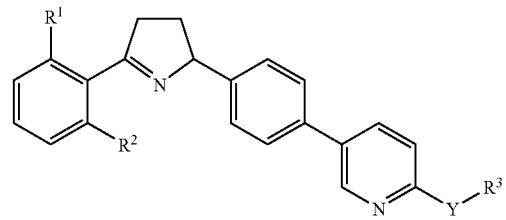

in which $R^1$, $R^2$, Y and $R^3$ are as defined in the disclosure, to a number of processes for preparing these substances, and to their use for controlling pests.

13 Claims, No Drawings

OTHER PUBLICATIONS

Synthesis, No. 7, (month unavailable) 1999, pp. 1163-1168, Isabelle Parrot et al, "Synthesis of Substituted 3-Amino-6-arylpyridazines via Suzuki Reaction".

Tetrahedron Lett., 40, (month unavailable) 1999, pp. 7975-7978, Isabelle Parrot et al, "Resin-bound thiophenols as $S_NAR$-labile linkers: application to the solid phase synthesis of aminopyridazines".

Tetrahedron Lett., vol. 37, No. 26, (month unavailable) 1996, pp. 4447-4450, Charles Z. Ding et al, "Synthesis of 4-(N-Alkyl-N-Heteroaryl)amino-3,4-Dihydro-3-Hydroxy-2,2-Dimethyl-2H-1-Benzopyran-6-Carbonitrile Derivatives via an Unusual 1,4-Oxygen to Nitrogen Heteroaryl Migration".

Tetrahedron Lett., 41, (month unavailable) 2000, pp. 4335-4338, Xin Wang et al, "Selective monolithiation of 2,5-dibromopyridine with butyllithium".

J. Org. Chem., 60, (month unavailable) 1995, pp. 7508-7510, Tatsuo Ishiyama et al, "Palladium(O)-Catalyzed Cross-Coupling Reaction of Alkoxydiboron with Haloarenes: A Direct Procedure for Arylboronic Esters".

Tetrahedron Lett,. vol. 38, No. 19, (month unavailable) 1997, pp. 3477-3478, Hesheng Zhang et al, "A Suite of Odd and Even Carbon-Numbered Spiroacetals in *Bactrocera latifrons*. Synthesis and Stereochemistry".

Chem. Ind., 37, (month unavailable) 1985, pp. 730-732, Harry R. Ungerer, "Schiffsfarben—eine Spezialität der seenahen Lackindustrie".

Tetrahedron Lett., 36, (month unavailable) 1995, pp. 9085-9088, Stephen A. Hitchcock et al, "Selectivity in Palladium(0)-Catalyzed Cross-Coupling Reactions: Application to a Tandem Stille Reaction".

$\Delta^1$-PYRROLINES

The present patent application has been filed under 35 U.S.C. 371 as a national stage application of PCT/EP02/12259, filed Nov. 4, 2002, which was published in German as International Patent Publication WO 03/0401130 on May 15, 2003, which is entitled to the right of priority of German Patent Application 101 54 515.0, filed Nov. 7, 2001.

The present invention relates to novel $\Delta^1$-pyrrolines, to a number of processes for them, and to their use as pesticides.

It is already known that many $\Delta^1$-pyrrolines possess insecticidal properties (cf. WO 00/21958, WO 99/59968, WO 99/59967 and WO 98/22438). The activity of these substances, although good, leaves a certain amount to be desired in some cases.

The invention now provides novel $\Delta^1$-pyrrolines of the formula (I)

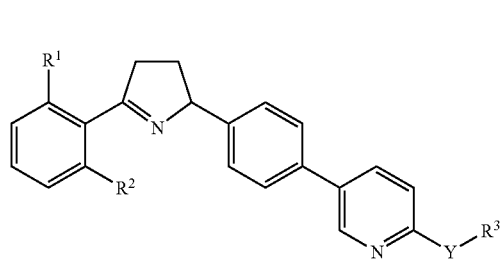

in which
R$^1$ is halogen or methyl,
R$^2$ is hydrogen or halogen,
Y is O (oxygen) or S (sulphur),
R$^3$ is $C_1$–$C_4$-alkyl, $C_3$–$C_6$-cycloalkyl or $C_3$–$C_6$-cycloalkyl-$C_1$–$C_2$-alkyl.

Depending on the type and number of substituents, the compounds of the formula (I) may where appropriate be present in the form of geometrical and/or optical isomers or regioisomers or isomer mixtures thereof in varying compositions. Both the pure isomers and the isomer mixtures are claimed by the invention.

It has additionally been found that $\Delta^1$-pyrrolines of the formula (I) can be prepared by a process in which A) $\Delta^1$-pyrrolines of the formula (II)

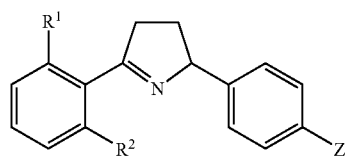

in which
R$^1$ and R$^2$ are as defined above and
Z is chlorine, bromine, iodine, —OSO$_2$CF$_3$ or —OSO$_2$(CF$_2$)$_3$CF$_3$,
are reacted in a tandem reaction with heterocycles of the formula (III)

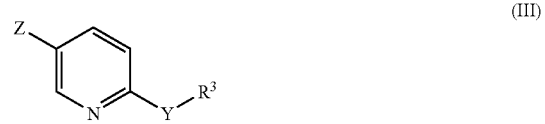

in which
Y and R$^3$ are as defined above and
X is chlorine, bromine, iodine, —OSO$_2$CF$_3$ or —OSO$_2$(CF$_2$)$_3$CF$_3$, in the presence of a catalyst, in the presence of a diboronic ester and, where appropriate, in the presence of an acid binder and, where appropriate, in the presence of a diluent or B) $\Delta^1$-pyrrolines of the formula (IV)

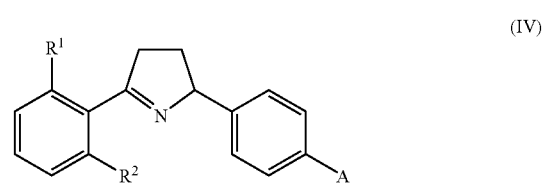

in which
R$^1$ and R$^2$ are as defined above and
A is —B(OH)$_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxabo-rinan)-2-yl or 1,3,2-benzo-dioxaborol-2-yl,
are reacted with heterocycles of the formula (III)

in which
Y, R$^3$ and X are as defined above
in the presence of a catalyst, where appropriate in the presence of an acid binder and where appropriate in the presence of a diluent, or C) $\Delta^1$-pyrrolines of the formula (II)

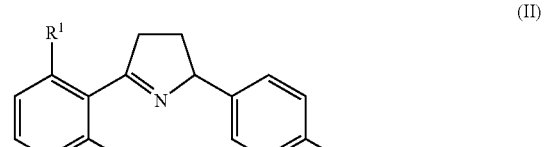

in which

R$^1$, R$^2$ and Z are as defined above, are reacted with boronic acid derivatives of the formula (V)

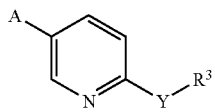
(V)

in which

Y, R$^3$ and A are as defined above, in the presence of a catalyst, where appropriate in the presence of an acid binder and where appropriate in the presence of a diluent or D) Δ$^1$-pyrrolines of the formula (II-a)

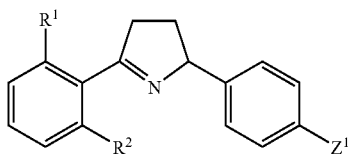
(II-a)

in which

R$^1$ and R$^2$ are as defined above,

Z$^1$ is bromine or iodine, are reacted with organometallic compounds of the formula (VI)

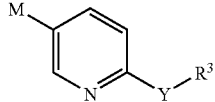
(VI)

in which

Y and R$^3$ are as defined above and,

M is ZnCl, Sn(Me)$_3$ or Sn(n-Bu)$_3$, in the presence of a catalyst, where appropriate in the presence of an acid binder and where appropriate in the presence of a diluent.

Finally, it has been found that the compounds of the formula (I) according to the invention possess very good insecticidal properties and can be used both in crop protection and in the protection of materials for controlling unwanted pests, such as insects.

A general definition of the Δ$^1$-pyrrolines of the invention is given by the formula (I).

Preferred Δ$^1$-pyrrolines are those of the formula (I), in which

R$^1$ is fluorine, chlorine or methyl,

R$^2$ is hydrogen, fluorine or chlorine,

Y is O (oxygen) or S (sulphur),

R$^3$ is C$_{1-4}$-alkyl, C$_{3-6}$-cycloalkyl or C$_{3-6}$-cycloalkyl-C$_{1-2}$-alkyl.

Particularly preferred Δ$^1$-pyrrolines of the formula (I) are those in which

R$^1$ is fluorine or chlorine,

R$^2$ is hydrogen, fluorine or chlorine,

Y is O (oxygen) or S (sulphur),

R$^3$ is methyl, ethyl, propyl, butyl, cyclopropyl, cyclobutyl, cyclopentyl, cyclohexyl, cyclopropyl-C$_{1-2}$-alkyl, cyclobutyl-C$_{1-2}$-alkyl, cyclopentyl-C$_{1-2}$-alkyl or cyclohexyl-C$_{1-2}$-alkyl.

Very particularly preferred Δ$^1$-pyrrolines of the formula (I) are those in which R$^1$ is fluorine or chlorine, R$^2$ is hydrogen or fluorine, Y is O (oxygen) or S (sulphur), R$^3$ is methyl, ethyl, n-propyl, iso-propyl, n-butyl, iso-butyl, sec-butyl, tert-butyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl or cyclohexylethyl.

Further preferred Δ$^1$-pyrrolines of the formula (I) are those in which R$^1$ and R$^2$ are fluorine.

Further preferred Δ$^1$-pyrrolines of the formula (I) are those in which Y is oxygen.

Further preferred Δ$^1$-pyrrolines of the formula (I) are those in which Y is sulphur.

Further preferred Δ$^1$-pyrrolines of the formula (I) are those in which R$^3$ is C$_1$–C$_4$-alkyl.

Very particular preference is given to (R)-configured compounds of the formula (I-a)

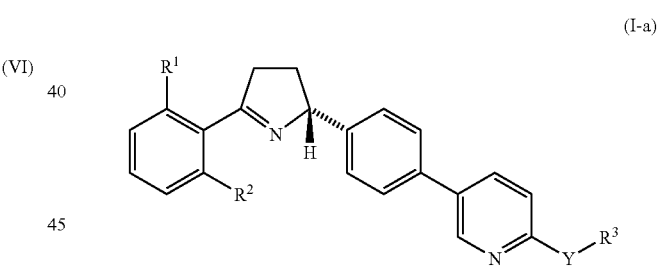
(I-a)

in which

R$^1$, R$^2$, Y and R$^3$ are as defined above.

Compounds of the formula (I-a) are obtained by conventional methods of racemate cleavage, such as, for example, by chromatography of the corresponding racemates on a chiral stationary phase. In this way it is possible to break down either the racemic end products or racemic intermediates into the two enantiomers.

Saturated hydrocarbon radicals such as alkyl may where possible in each case be straight-chain or branched.

The general definitions of radicals and elucidations set out above, or those set out in ranges of preference, may also, however, be combined with one another, thus including any combinations between the respective ranges and the ranges of preference. They apply correspondingly to the end products and also to the precursors and intermediates.

Using 5-(2,6-difluorophenyl)-2-(4-bromophenyl)-3,4-dihydro-2H-pyrrole, N-5-bromo-2-ethoxy-pyridine and 4,4,4',4',5,5,5',5'-octamethyl-2,2'-bi-1,3,2-dioxaborolane as starting materials, plus a palladium catalyst, the course of process (A) of the invention can be illustrated by the following formula scheme.

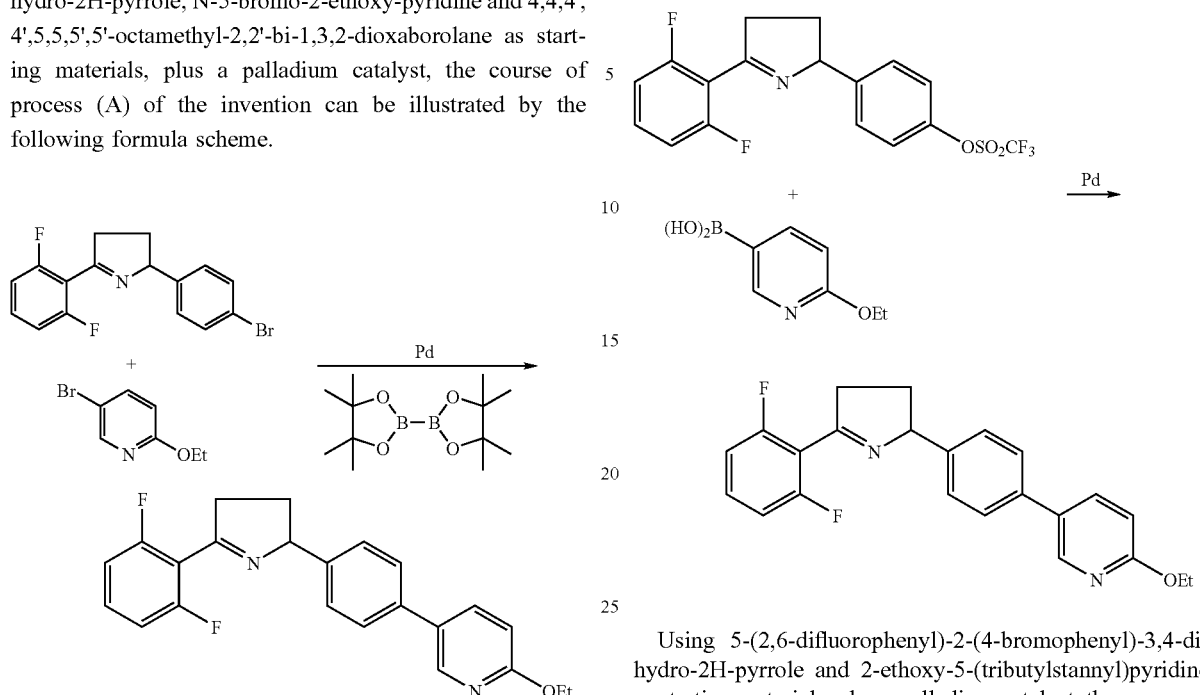

Using 5-(2,6-difluorophenyl)-2-[4-(4,4,5,5-tetramethyl-1,3,2-dioxaborolan-2-yl)-phenyl]-3,4-dihydro-2H-pyrrole and 5-bromo-2-isopropoxy-pyridine as starting materials, plus a palladium catalyst, the course of process (B) of the invention can be illustrated by the following formula scheme.

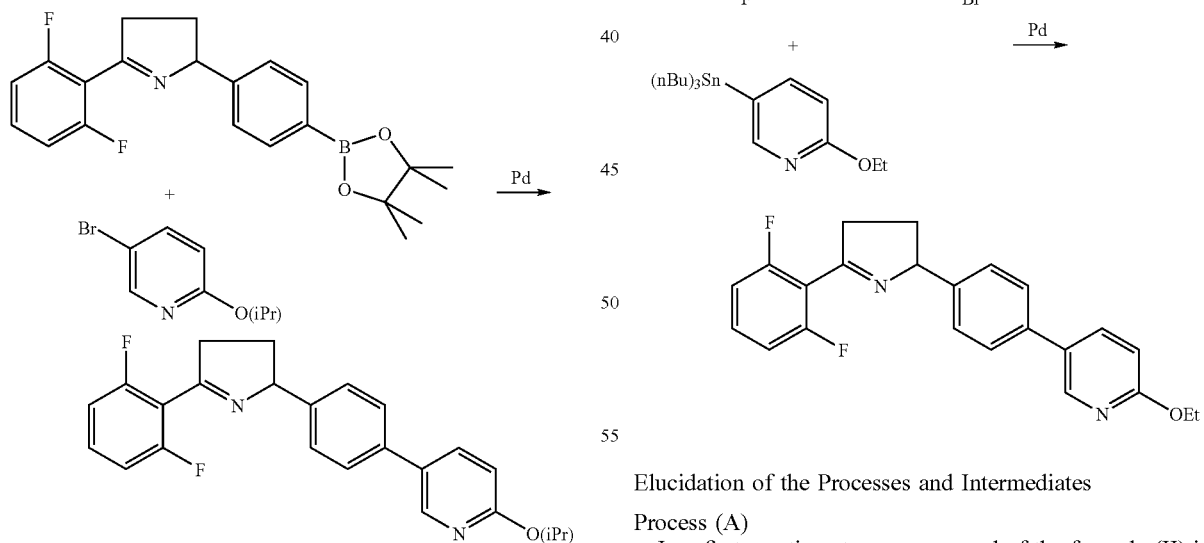

Using 5-(2,6-difluorophenyl)-2-[4-(trifluoromethylsulphonyloxy)phenyl]-3,4-dihydro-2H-pyrrole and 2-ethoxy-5-pyridinylboronic acid as starting materials, plus a palladium catalyst, the course of process (C) of the invention can be illustrated by the following formula scheme.

Using 5-(2,6-difluorophenyl)-2-(4-bromophenyl)-3,4-dihydro-2H-pyrrole and 2-ethoxy-5-(tributylstannyl)pyridine as starting materials, plus a palladium catalyst, the course of process (D) of the invention can be illustrated by the following formula scheme.

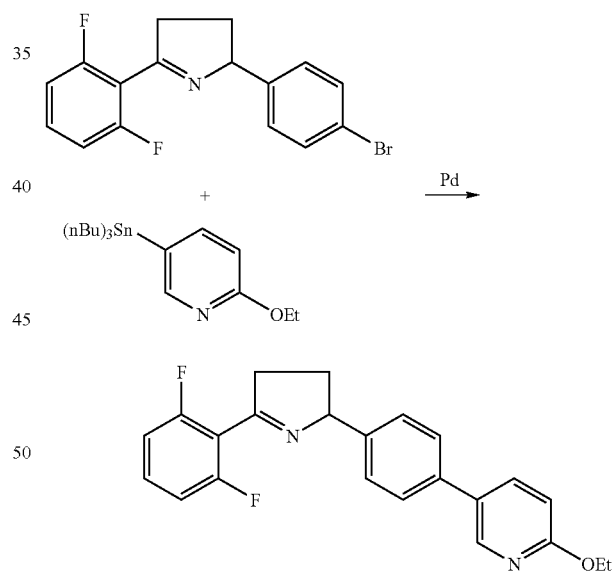

Elucidation of the Processes and Intermediates

Process (A)

In a first reaction step a compound of the formula (II) is coupled with a diboronic ester in the presence of a palladium catalyst, where appropriate in the presence of an acid binding agent and where appropriate in the presence of a solvent. In a second reaction step, without isolating the intermediate and in the same reaction vessel, a compound of the formula (III) is coupled in the presence of a catalyst, where appropriate in the presence of an acid binding agent and where appropriate in the presence of a solvent (cf. e.g. Tetrahedron Lett. 1997, 38, 3841).

Process (A) of the invention can be conducted in two variants. Either a compound of the formula (II) or a compound of the formula (III) can be introduced initially. Process (A) can be regarded as a tandem reaction of processes (B) and (C) described below.

A general definition of the $\Delta^1$-pyrrolines required as starting materials when carrying out process A of the invention is given by the formula (II). In this formula $R^1$ and $R^2$ stand preferably, with particular preference or with very particular preference for those definitions which have already been given as preferred, particularly preferred, etc. for these radicals in connection with the description of the substances of the formula (I) according to the invention. Z is preferably bromine, iodine, —OSO$_2$CF$_3$ or —OSO$_2$(CF$_2$)$_3$CF$_3$, with particular preference bromine, —OSO$_2$CF$_3$ or —OSO$_2$(CF$_2$)$_3$CF$_3$, with very particular preference bromine or —OSO$_2$CF$_3$.

$\Delta^1$-Pyrrolines of the formula (II) can be prepared by known processes (cf. WO 98/22438).

A general definition of the heterocycles required as starting materials when carrying out process (A) of the invention is given by the formula (III). In this formula Y and $R^3$ stand preferably, with particular preference or with very particular preference for those meanings which were already mentioned as preferred, particularly preferred, etc. for these radicals in connection with the description of the substances of the formula (I) according to the invention. X is preferably bromine, chlorine, iodine or —OSO$_2$CF$_3$, with particular preference bromine, chlorine or iodine, with very particular preference bromine or chlorine.

The heterocycles of the formula (III) are known or can be prepared by known processes (cf. Aust. J. Chem. 1964, 17, 794; Chem. Ber. 1992, 125, 1169; Chem. Pharm. Bull. 1995, 43, 247; Eur. J. Med. Chem. 1989, 24, 249; J. Chem. Soc. C 1971, 1889; J. Chem. Soc. Perkin Trans. 1 1995, 2497; J. Med. Chem. 1991, 34, 315; J. Org. Chem. 1984, 49, 2240; J. Org. Chem. 1990, 55, 69; Org. Prep. Proced. Int. 1998, 30, 433; Synthesis 1999, 1163; Tetrahedron 1999, 40, 7975; Tetrahedron Lett. 1996, 37, 4447; Tetrahedron Lett. 2000, 41, 4335).

Suitable diboronic esters when carrying out process (A) of the invention include 4,4,4',4',5,5,5',5'-octamethyl-2,2'-bi-1,3,2-dioxaborolane, 5,5,5',5'-tetramethyl-2,2'-bi-1,3,2-dioxaborinane, 4,4,4',4',6,6'-hexamethyl-2,2'-bi-1,3,2-dioxaborinane or 2,2'-bi-1,3,2-benzodioxaborole. Preference is given to using 4,4,4',4',5,5,5',5'-octamethyl-2,2'-bi-1,3,2-dioxaborolane, 5,5,5',5'-tetramethyl-2,2'-bi-1,3,2-dioxaborinane or 4,4,4',4',6,6'-hexamethyl-2,2'-bi-1,3,2-dioxaborinane, with particular preference 4,4,4',4',5,5,5',5'-octamethyl-2,2'-bi-1,3,2-dioxaborolane or 5,5,5',5'-tetramethyl-2,2'-bi-1,3,2-dioxaborinane, with very particular preference 4,4,4',4',5,5,5',5'-octamethyl-2,2'-bi-1,3,2-dioxaborolane.

Process (A) of the invention is carried out using generally 1 mol or a slight excess of a diboronic ester and 1 mol or a slight excess of a compound of the formula (III) per mole of compound of the formula (II), plus 3% of a palladium catalyst. It is also possible, however, to use the reaction components in other proportions. Either the compound of the formula (II) or the compound of the formula (III) can be introduced initially. Working up takes place by conventional methods. The general procedure is to dilute the reaction mixture with water and subject it to extraction with ethyl acetate. The organic phase is washed, dried, filtered and concentrated. The residue is freed where appropriate from any impurities still present by conventional methods, such as chromatography or recrystallization.

Process (B)

A general definition of the $\Delta^1$-pyrrolines required as starting materials when carrying out process (B) of the invention is given by the formula (IV). In this formula $R^1$ and $R^2$ stand preferably, with particular preference or with very particular preference for those definitions which have already been mentioned as preferred, particularly preferred, etc. for these radicals in connection with the description of the substances of the formula (I) according to the invention. A is preferably (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, with particular preference (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, with very particular preference (4,4,5,5-tetramethyl-1,3,2-dioxaborolan)-2-yl, (5,5-dimethyl-1,3,2-dioxaborinan)-2-yl.

$\Delta^1$-Pyrrolines of the formula (IV) can be prepared by reacting a) compounds of the formula (II)

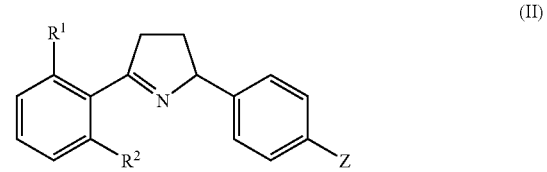

(II)

in which $R^1$, $R^2$ and Z are as defined above with a diboronic ester in the presence of a catalyst, where appropriate in the presence of an acid binder and where appropriate in the presence of a diluent (cf. J. Org. Chem. 1995, 60, 7508; Tetrahedron Lett. 1997, 38, 3447).

Suitable diboronic esters for carrying out process (a) were mentioned above in connection with the description of process (A) of the invention.

The heterocycles of the formula (III) required as starting materials when carrying out process (B) of the invention have already been described above in connection with the description of process (A).

When carrying out process (B) of the invention generally 1 mol or a slight excess of a compound of the formula (III) is used per mole of compound of the formula (V). It is also possible, however, to use the reaction components in other proportions. Working up takes place by customary methods. The general procedure is to take up the reaction mixture in ethyl acetate and to wash the organic phase with water, dry it over sodium sulphate, filter it and concentrate the filtrate. The residue is where appropriate freed from any impurities that are still present by customary methods, such as chromatography or recrystallization.

Process (C)

The Δ¹-pyrrolines of the formula (II) required as starting materials when carrying out process (C) of the invention have already been described in connection with the description of process (A).

The general definition of the boronic acid derivatives required as starting materials when carrying out process (C) of the invention is given by the formula (V). In this formula Y and $R^3$ stand preferably, with particular preference or with very particular preference for those definitions which have already been mentioned as being preferred, particularly preferred, etc. for these radicals in connection with the description of the substances of the formula (I) according to the invention. A is preferably (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxa-borol-2-yl, with particular preference (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, with very particular preference (4,4,5,5-tetramethyl-1,3,2-dioxaborolan)-2-yl, (5,5-dimethyl-1,3,2-dioxaborinan)-2-yl.

The compounds of the formula (V) are known or can be prepared by known processes (cf. J. Org. Chem. 1995, 60, 7508, Tetrahedron Lett. 1997, 38, 3447).

When carrying out process (C) of the invention generally 1 mol or a slight excess of a compound of the formula (V) is used per mole of compound of the formula (II). It is also possible, however, to use the reaction components in different proportions. Working up takes place by customary methods. The general procedure is to take up the reaction mixture in ethyl acetate and to wash the organic phase with water, dry it over sodium sulphate, filter it and concentrate the filtrate. The residue is where appropriate freed from any impurities still present by customary methods, such as chromatography or recrystallization.

Process (D)

A general definition of the Δ¹-pyrrolines required as starting materials when carrying out process (D) of the invention is given by the formula (II-a). In this formula $R^1$ and $R^2$ stand preferably, with particular preference or with very particular preference for those definitions which have already been mentioned as being preferred, particularly preferred, etc. for these radicals in connection with the description of the substances of the formula (I) according to the invention. $Z^1$ is preferably bromine or iodine.

Δ¹-Pyrrolines of the formula (II-a) can be prepared by known processes (cf. WO 98/22438).

A general definition of the organometallic compounds required as starting materials when carrying out process (D) of the invention is given by the formula (VI). In this formula Y and $R^3$ stand preferably, with particular preference or with very particular preference for those definitions which have already been mentioned as being preferred, particularly preferred, etc. for these radicals in connection with the description of the substances of the formula (I) according to the invention. M is preferably ZnCl, Sn(Me)₃ or Sn(n-Bu)₃.

Organometallic compounds of the formula (VI) are known in some cases or can be prepared by known methods. It is possible, for example, to prepare compounds of the formula (VI) in situ from the corresponding compounds of the formula (III) in which X is —OSO₂CF₃, (cf. Tetrahedron Lett. 1995, 36, 9085).

When carrying out process (D) of the invention generally 1 mol or a slight excess of a compound of the formula (VI) is used per mole of compound of the formula (II-a). It is also possible, however, to use the reaction components in different proportions. Working up takes place in accordance with customary methods. The general procedure is to take up the reaction mixture in ethyl acetate and to wash the organic phase with water, dry it over sodium sulphate, filter it and concentrate the filtrate. The residue is freed where appropriate from any impurities still present by customary methods, such as chromatography or recrystallization.

Chiral Compounds of the Formula (I-a)

Chiral compounds of the formula (I-a) can be prepared, for example, by subjecting Δ¹-pyrrolines of the formula (II-b)

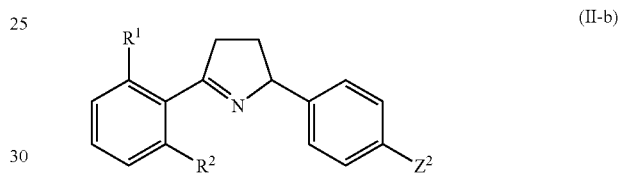

(II-b)

in which $R^1$ and $R^2$ are as defined above and $Z^2$ is chlorine, bromine or iodine, to racemate cleavage. This is done by working, for example, in accordance with methods of preparative chromatography, preferably by the method of high performance liquid chromatography (HPLC). A chiral stationary silica gel phase is used. A silica gel modified with tris(3,5-dimethylphenylcarbamate)-cellulose has proven to be particularly suitable for resolving the compounds of the formula (II-b) into the two enantiomers. This separation material is available commercially. It is also possible, however, to use other stationary phases. Suitable mobile phases include all customary inert, organic solvents, and also mixtures thereof. Preferred possibilities for use include optionally halogenated aliphatic, alicyclic or aromatic hydrocarbons, such as petroleum ether, hexane, heptane, cyclohexane; dichloromethane, chloroform; alcohols, such as methanol, ethanol, propanol; nitriles, such as acetonitrile; esters such as methyl acetate or ethyl acetate. Particular preference is given to using aliphatic hydrocarbons, such as hexane or heptane, and alcohols, such as methanol or propanol; very particular preference is given to n-heptane and isopropanol or mixtures thereof. Operation is generally carried out at temperatures between 10° C. and 60° C., preferably between 10° C. and 40° C., with particular preference at room temperature. The (R)-configured enantiomers obtained in this way are then used as starting materials for processes (A), (C) or (D).

When carrying out processes (A), (B), (C) and (D) of the invention in each case a palladium catalyst is used which can be employed with or without the addition of further ligands.

As the catalyst it is preferred to use PdCl$_2$(dppf) [dppf=1,1'-bis(diphenylphosphino)ferrocene], Pd(PPh$_3$)$_4$, PdCl$_2$(PPh$_3$)$_2$, PdCl$_2$(CH$_3$CN)$_2$, Pd$_2$(dba)$_3$ [dba=dibenzylideneacetone] or Pd(OAc)$_2$, with particular preference PdCl$_2$(dppf), Pd(PPh$_3$)$_4$, PdCl$_2$(PPh$_3$)$_2$, or Pd(OAc)$_2$, with very particular preference PdCl$_2$(dppf) or PdCl$_2$(PPh$_3$)$_2$.

Suitable ligands include triarylphosphines, trialkylphosphines or arsines. Preference is given to using dppf, PPh$_3$, P(tert-Bu)$_3$, Pcy$_3$ or AsPh$_3$, with particular preference dppf.

Suitable diluents when carrying out processes (A), (B) and (C) of the invention include all customary inert organic solvents. Preferred possibilities for use are optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methyl-formanilide, N-methylpyrrolidone or hexamethylphosphoramide; esters such as methyl acetate or ethyl acetate, sulphoxides, such as dimethyl sulphoxide, or sulphones, such as sulpholane. Particular preference is given to using acetone, di-methoxyethane, dioxane, tetrahydrofuran, dimethylformamide, dimethylacetamide, dimethyl sulphoxide, ethanol, toluene or, where appropriate, mixtures of these stated diluents with water.

Suitable diluents when carrying out process (D) of the invention include all customary inert organic solvents. Preferred possibilities for use are optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, tetrachloromethane, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole. Particular preference is given to using dioxane, tetrahydrofuran or toluene.

Suitable acid binding agents when carrying out the processes (A), (B), (C) and (D) of the invention include in each case all organic and inorganic bases that are customary for such reactions. Preferred possibilities for use are alkaline earth metal hydroxides or alkali metal hydroxides, such as sodium hydroxide, calcium hydroxide or potassium hydroxide, or else ammonium hydroxide, alkali metal carbonates, such as sodium carbonate, potassium carbonate, potassium hydrogen carbonate, sodium hydrogen carbonate, alkali metal acetates or alkaline earth metal acetates such as sodium acetate, potassium acetate, calcium acetate, alkali metal fluorides, and also tertiary amines, such as trimethylamine, triethylamine, tributylamine, N,N-dimethyl-aniline, pyridine, N-methylpiperidine, N,N-dimethylaminopyridine, diazabicyclo-octane (DABCO), diazabicyclononene (DBN) or diazabicycloundecene (DBU). It is also possible, however, to operate without additional acid binder, or to use the amine component in excess, so that it functions simultaneously as an acid binder. Particular preference is given to using barium hydroxide, sodium hydroxide, potassium hydroxide, tripotassium phosphate, caesium carbonate, potassium carbonate, sodium carbonate, potassium acetate, triethylamine, potassium tert-butoxide, caesium fluoride or potassium fluoride.

The reaction temperatures when carrying out processes (A), (B) and (C) of the invention can in each case be varied within a relatively wide range. They are generally carried out at temperatures between 0° C. and 140° C., preferably between 20° C. and 120° C., with particular preference between 60° C. and 100° C.

The reaction temperatures when carrying out process (D) of the invention can in each case be varied within a relatively wide range. It is generally carried out at temperatures between 0° C. and 140° C., preferably between 20° C. and 120° C., All processes of the invention are generally carried out under atmospheric pressure. It is also possible, however, to operate under increased pressure or reduced pressure in each case.

The active compounds are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria* migratorioides, *Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius*, *Piesma quadrata*, *Cimex lectularius*, *Rhodnius prolixus* and *Triatoma* spp.

From the order of the Homoptera, for example, *Aleurodes brassicae*, *Bemisia tabaci*, *Traleurodes vaporariorum*, *Aphis gossypii*, *Brevicoryne brassicae*, *Cryptomyzus ribis*, *Aphis fabae*, *Aphis pomi*, *Eriosoma lanigerum*, *Hyalopterus arundinis*, *Phylloxera vastatrix*, *Pemphigus* spp., *Macrosiphum avenae*, *Myzus* spp., *Phorodon humuli*, *Rhopalosiphum padi*, *Empoasca* spp., *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus* spp. and *Psylla* spp.

From the order of the Lepidoptera, for example, *Pectinophora gossypiella*, *Bupalus piniarius*, *Cheimatobia brumata*, *Lithocolletis blancardella*, *Hyponomeuta padella*, *Plutella xylostella*, *Malacosoma neustria*, *Euproctis chrysorrhoea*, *Lymantria* spp., *Bucculatrix thurberiella*, *Phyllocnistis citrella*, *Agrotis* spp., *Euxoa* spp., *Feltia* spp., *Earias insulana*, *Heliothis* spp., *Mamestra brassicae*, *Panolis flammea*, *Spodoptera* spp., *Trichoplusia ni*, *Carpocapsa pomonella*, *Pieris* spp., *Chilo* spp., *Pyrausta nubilalis*, *Ephestia kuehniella*, *Galleria mellonella*, *Tineola bisselliella*, *Tinea pellionella*, *Hoffmannophila pseudospretella*, *Cacoecia podana*, *Capua reticulana*, *Choristoneura fumiferana*, *Clysia ambiguella*, *Homona magnanima*, *Tortrix viridana*, *Cnaphalocerus* spp., *Oulema oryzae*.

From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptinotarsa decemlineata*, *Phaedon cochleariae*, *Diabrotica* spp., *Psylliodes chrysocephala*, *Epilachna varivestis*, *Atomaria* spp., *Oryzaephilus surinamensis*, *Anthonomus* spp., *Sitophilus* spp., *Otiorrhynchus sulcatus*, *Cosmopolites sordidus*, *Ceuthorrhynchus assimilis*, *Hypera postica*, *Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp., *Brevipalpus* spp.

The phytoparasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

In particular, the compounds of the formula (I) according to the invention have excellent activity against caterpillars, beetle larvae, spider mites, aphids and leaf-mining flies.

The substances of the invention additionally display a very good duration of action, such as against the caterpillars of the cotton budworm (*Heliothis virescens*) or the caterpillars of the armyworm (*Spodoptera frugiperda*).

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds according to the invention with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations as a mixture with known fungicides, bactericides, acaracides, nematicides or insecticides, in order, for example, to increase the spectrum of activity or to prevent the development of resistance. In many cases synergistic effects are thus achieved, ie the efficacy of the mixture is greater than the efficacy of the individual components.

Particularly advantageous co-components are, for example, the following:

Fungicides:

aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, carpropamide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenhexamide, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), quinoxyfen, sulphur and sulphur preparations, spiroxamine, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-β-propyl-1H-1,2,4-triazole-1-ethanol, α-(2,4-dichlorophenyl)-β-methoxy-α-methyl-1H-1,2,4-triazole-1-ethanol, α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran-3'-one,
4-[3,4-dimethoxyphenyl)-3-(4-fluorophenyl)-acryloyl]-morpholine Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypernethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, omethoate, oxamyl, oxydemethon M, Paecilomyces fumosoroseus, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulphotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N '-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate N-cyanomethyl-4-trifluoromethyl-nicotinamide 3,5-dichloro-1-(3,3-dichloro-2-propenyloxy)-4-[3-(5-trifluoromethylpyridin-2-yloxy)-propoxy]-benzene It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. By plant cultivars are meant plants having new properties ("traits"), bred either by conventional breeding, by mutagenesis or by recombinant DNA techniques. They may be cultivars, biotypes and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The preferred transgenic plants or plant cultivars (i.e. those obtained by genetic engineering) which are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from Bacillus thuringiensis (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are increased defence of plants against fungi, bacteria and viruses by systematic acquired resistance (SAR), systemine, phytoalexins, elicitors and resistance genes and corresponding expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticonis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootennopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agents according to the invention or mixtures comprising these are to be understood as meaning, for example:

building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/-styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae.*

From the order of the Araneae, for example, *Aviculariidae* and *Araneidae.*

From the order of the Opiliones, for example, *Pseudoscorpiones chelifer, Pseudoscorpiones cheiridium* and *Opiliones phalangium.*

From the order of the Isopoda, for example, *Oniscus asellus* and *Porcellio scaber.*

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa.*

From the order of the Saltatoria, for example, *Acheta domesticus.*

From the order of the Dermaptera, for example, *Forficula auricularia.*

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae*, *Necrobia* spp., *Ptinus* spp., *Rhizopertha dominica*, *Sitophilus granarius*, *Sitophilus oryzae*, *Sitophilus zeamais* and *Stegobium paniceum*.

From the order of the Diptera, for example, *Aedes aegypti*, *Aedes albopictus*, *Aedes taeniorhynchus*, *Anopheles* spp., *Calliphora erythrocephala*, *Chrysozona pluvialis*, *Culex quinquefasciatus*, *Culex pipiens*, *Culex tarsalis*, *Drosophila* spp., *Fannia canicularis*, *Musca domestica*, *Phlebotomus* spp., *Sarcophaga carnaria*, *Simulium* spp., *Stomoxys calcitrans* and *Tipula paludosa*.

From the order of the Lepidoptera, for example, *Achroia grisella*, *Galleria mellonella*, *Plodia interpunctella*, *Tinea cloacella*, *Tinea pellionella* and *Tineola bisselliella*.

From the order of the Siphonaptera, for example, *Ctenocephalides canis*, *Ctenocephalides felis*, *Pulex irritans*, *Tunga penetrans* and *Xenopsylla cheopis*.

From the order of the Hymenoptera, for example, *Camponotus herculeanus*, *Lasius fuliginosus*, *Lasius niger*, *Lasius umbratus*, *Monomorium pharaonis*, *Paravespula* spp. and *Tetramorium caespitum*.

From the order of the Anoplura, for example, *Pediculus humanus capitis*, *Pediculus humanus corporis* and *Phthirus pubis*.

From the order of the Heteroptera, for example, *Cimex hemipterus*, *Cimex lectularius*, *Rhodinus prolixus* and *Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

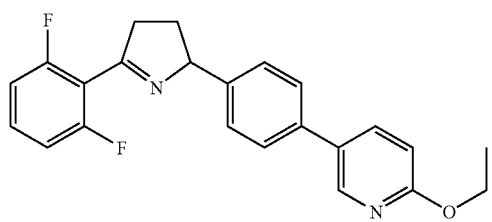

5-(2,6-Difluorophenyl)-2-[4-(4,4,5,5-tetramethyl-1,3,2-dioxaborolan-2-yl)phenyl]-3,4-dihydro-2H-pyrrole (0.96 g, 2.50 mmol) is introduced in 1,2-dimethoxyethane (70 ml) under an argon atmosphere. Added in succession are 5-bromo-2-ethoxypyridine (III-1) (0.61 g, 3.00 mmol), 1,1'-bis(diphenylphosphino)ferrocenepalladium(II) chloride (0.05 g, 0.07 mol) and 3.75 ml of sodium carbonate solution (20% strength, w/v). The reaction mixture is allowed to continue reaction at 80° C. for 16 h.

Thereafter, water/ethyl acetate are added to the reaction mixture and the organic phase is separated off, dried over sodium sulphate, filtered, mixed with 5 g of Florisil and concentrated. The crude product is purified by chromatography on silica gel (mobile phase: n-hexane/ethyl acetate 4:1).

This gives 0.68 g (67% of theory) of 5-{4-[5-(2,6-difluorophenyl)-3,4-dihydro-2H-pyrrol-2-yl]phenyl}-2-ethoxypyridine.

HPLC: logP (pH 2.3)=2.92 NMR (CD$_3$CN): δ=1.3–1.4 (t, 3H), 1.8–1.9 (m, 1H), 2.7 (m, 1H), 3.0–3.1 (m, 2H), 4.3–4.4 (m, 2H), 5.3 (m, 1H), 6.8 (d, 1H), 7.0–7.1 (t, 2H), 7.3–7.4 (m, 3H), 7.4 (d, 2H), 7.9 (m, 1H), 8.4 (d, 1H) ppm.

In analogy to Example 1 and in accordance with the general descriptions of processes (A), (B), (C) or (D) the compounds listed in the table below can be prepared.

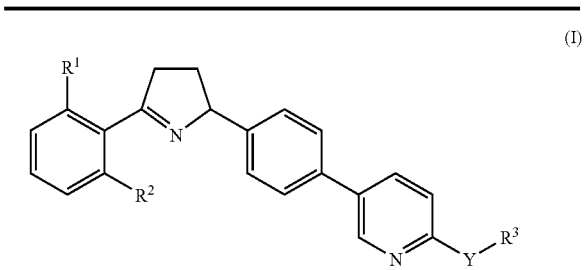

(I)

| No. | R$^1$ | R$^2$ | Y | R$^3$ | log P |
|---|---|---|---|---|---|
| 2 | F | F | O | Methyl | |
| 3 | F | F | S | Methyl | |
| 4 | F | F | S | Ethyl | 3.29[a)], 4.54[b)] |
| 5 | F | F | O | n-Propyl | 3.42[a)], 4.77[b)] |
| 6 | F | F | S | n-Propyl | |
| 7 | F | F | O | i-Propyl | 3.42[a)], 4.73[b)] |
| 8 | F | F | S | i-Propyl | 3.80[a)], 4.96[b)] |
| 9 | F | F | O | n-Butyl | |
| 10 | F | F | S | n-Butyl | |
| 11 | F | F | O | i-Butyl | |
| 12 | F | F | S | i-Butyl | |
| 13 | F | F | O | s-Butyl | |
| 14 | F | F | S | s-Butyl | |
| 15 | F | F | O | t-Butyl | 3.94[a)] |
| 16 | F | F | S | t-Butyl | |
| 17 | F | F | O | Cyclopropyl | |
| 18 | F | F | S | Cyclopropyl | |
| 19 | F | F | O | Cyclobutyl | 3.66[a)], 4.90[b)] |
| 20 | F | F | S | Cyclobutyl | |

-continued

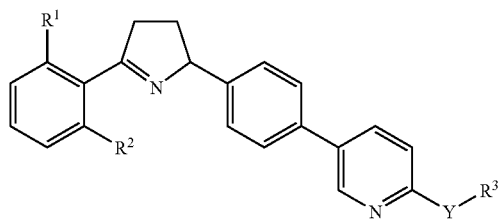

| No. | R¹ | R² | Y | R³ | log P |
|---|---|---|---|---|---|
| 21 | F | F | O | Cyclopentyl | 3.99[a], 5.34[b] |
| 22 | F | F | S | Cyclopentyl | |
| 23 | F | F | O | Cyclohexyl | |
| 24 | F | F | S | Cyclohexyl | |
| 25 | F | F | O | Cyclopropylmethyl | 3.48[a], 4.67[b] |
| 26 | F | F | S | Cyclopropylmethyl | |
| 27 | F | F | O | Cyclobutylmethyl | |
| 28 | F | F | S | Cyclobutylmethyl | |
| 29 | F | F | O | Cyclopentylmethyl | |
| 30 | F | F | S | Cyclopentylmethyl | |
| 31 | F | F | O | Cyclohexylmethyl | |
| 32 | F | F | S | Cyclohexylmethyl | |
| 33 | F | F | O | Cyclopropylethyl | |
| 34 | F | F | S | Cyclopropylethyl | |
| 35 | F | F | O | Cyclobutylethyl | |
| 36 | F | F | S | Cyclobutylethyl | |
| 37 | F | F | O | Cyclopentylethyl | |
| 38 | F | F | S | Cyclopentylethyl | |
| 39 | F | F | O | Cyclohexylethyl | |
| 40 | F | F | S | Cyclohexylethyl | |

Preparation of Starting Materials of the Formula (III)

Example III-1

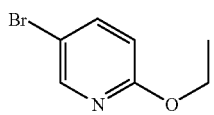

0.49 g (20.26 mmol) of sodium hydride is introduced under argon and cooled to 10° C. 10 ml of dimethylformamide are added. Subsequently a solution of 0.93 g (20.26 mmol) of ethanol in 40 ml of dimethylformamide is added slowly dropwise and reaction is allowed to continue for 30 minutes. Thereafter 4.00 g (16.89 mmol) of 2,5-dibromopyridine are added dropwise and reaction is allowed to continue for a further 16 hours.

Water is added to the reaction mixture. It is extracted three times with ethyl acetate. The organic phase is washed once with sodium hydrogen carbonate solution and once with sodium chloride solution, dried over sodium sulphate, filtered and concentrated.

This gives 2.35 g (67% of theory) of 5-bromo-2-ethoxypyridine.

HPLC: logP (pH 2.3)=2.92 NMR (CD₃CN): δ=1.33 (t, 3H), 4.27–4.32 (m, 2H), 6.68 (d, 1H), 7.75 (m, 1H), 8.2 (d, 1H) ppm.

The log p values reported in the above tables and preparation examples are determined in accordance with EEC Directive 79/831 Annex V.A8 by means of HPLC (high performance liquid chromatography) on a reversed-phase column (C 18). Temperature: 43° C.

Determination is carried out in the acidic range at a pH of 2.3 using 0.1% aqueous phosphoric acid and acetonitrile as mobile phases; linear gradient from 10% acetonitrile to 90% acetonitrile. The values are marked in the tables with [a].

Determination takes place in the neutral range at a pH of 7.5 with 0.01-molar aqueous phosphate buffer solution and acetonitrile as mobile phases; linear gradient from 10% acetonitrile to 90% acetonitrile. The values are marked in the tables with [b].

The calibration is carried out using unbranched alkan-2-ones (having from 3 to 16 carbon atoms) whose logP values are known (logP values determined on the basis of the retention times, using linear interpolation between two successive alkanones).

The lambda max values were determined in the maxima of the chromatographic signals using the UV spectra from 200 nm to 400 nm.

USE EXAMPLES

Example A

| Aphis gossypii test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids has been killed.

In this test, for example, the following compounds from the preparation examples display good activity:

TABLE A

Plant-damaging insects
*Aphis gossypii* test

| No. | Active compounds | Active compound concentration in ppm | Efficacy in % after $6^d$ |
|---|---|---|---|
| 5 | (structure) | 100 | 99 |
| 7 | (structure) | 100 | 99 |

Example B

| *Heliothis armigera* test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with caterpillars of the cotton bollworm (*Heliothis armigera*) whilst the leaves are still moist. After the desired period of time, the kill in % is determined. 100% means that all aphids have been killed; 0% means that none of the caterpillars has been killed.

In this test, for example, the following compounds from the preparation examples display good activity:

TABLE B

Plant-damaging insects
*Heliothis larvae* test

| No. | Active compounds | Active compound concentration in ppm | Efficacy in % after $7^d$ |
|---|---|---|---|
| 15 | (structure) | 20 | 100 |

TABLE B-continued

Plant-damaging insects
*Heliothis larvae* test

| No. | Active compounds | Active compound concentration in ppm | Efficacy in % after 7$^d$ |
|---|---|---|---|
| 25 | | 20 | 100 |

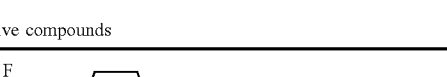

Example C

*Heliothis virescens* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*Glycine max*) are treated by being dipped into the preparation of active compound of the desired concentration and are populated with *Heliothis virescens* caterpillars whilst the leaves are still moist.

After the desired period of time, the kill in % is determined. 100% means that all caterpillars have been killed; 0% means that none of the caterpillars has been killed.

In this test, for example, the following compounds in the preparation examples display good activity:

TABLE C

Plant-damaging insects
*Heliothis virescens* test

| No. | Active compounds | Active compound concentration in ppm | Efficacy in % after 7$^d$ |
|---|---|---|---|
| 5 | | 100 | 100 |
| 4 | | 100 | 100 |

TABLE C-continued

Plant-damaging insects
*Heliothis virescens* test

| No. | Active compounds | Active compound concentration in ppm | Efficacy in % after 7$^d$ |
|---|---|---|---|
| 8 | [2,6-difluorophenyl-dihydropyrrole-phenyl-pyridine-S-isopropyl structure] | 100 | 100 |
| 7 | [2,6-difluorophenyl-dihydropyrrole-phenyl-pyridine-O-isopropyl structure] | 100 | 100 |

Example D

*Phaedon larvae* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) whilst the leaves are still moist.

After the desired period of time, the kill in % is determined. 100% means that all beetle larvae have been killed; 0% means that none of the beetle larvae has been killed.

In this test, for example, the following compounds from the preparation examples display superior activity as compared with the prior art:

TABLE D

Plant-damaging insects
*Phaedon larvae* test

| No. | Active compounds | Active compound concentration in ppm | Efficacy in % after 7$^d$ |
|---|---|---|---|
| 1 | [2,6-difluorophenyl-dihydropyrrole-phenyl-pyridine-O-ethyl structure] | 100 | 100 |

TABLE D-continued

*Plant-damaging insects*
*Phaedon larvae* test

| No. | Active compounds | Active compound concentration in ppm | Efficacy in % after 7$^d$ |
|---|---|---|---|
| 5 | 2,6-difluorophenyl-dihydropyrrole-phenyl-(6-propoxy)pyridine | 100 | 100 |
| 4 | 2,6-difluorophenyl-dihydropyrrole-phenyl-(6-ethylthio)pyridine | 100 | 100 |
| 8 | 2,6-difluorophenyl-dihydropyrrole-phenyl-(6-isopropylthio)pyridine | 100 | 100 |
| 7 | 2,6-difluorophenyl-dihydropyrrole-phenyl-(6-isopropoxy)pyridine | 100 | 100 |
| 15 | 2,6-difluorophenyl-dihydropyrrole-phenyl-(6-tert-butoxy)pyridine | 100 | 100 |
| 21 | 2,6-difluorophenyl-dihydropyrrole-phenyl-(6-cyclopentyloxy)pyridine | 100 | 100 |

TABLE D-continued

Plant-damaging insects
*Phaedon larvae* test

| No. | Active compounds | Active compound concentration in ppm | Efficacy in % after 7$^d$ |
|---|---|---|---|
| 25 | [structure: 2,6-difluorophenyl-dihydropyrrole-phenyl-pyridine-O-CH2-cyclopropyl] | 100 | 100 |
| 19 | [structure: 2,6-difluorophenyl-dihydropyrrole-phenyl-pyridine-O-cyclobutyl] | 20 | 100 |

Example E

*Plutella* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with cabbage moth (*Plutella xylostella*) caterpillars whilst the leaves are still moist.

After the desired period of time, the kill in % is determined. 100% means that all caterpillars have been killed; 0% means that none of the caterpillars has been killed.

In this test, for example, the following compounds from the preparation examples display good activity:

TABLE E

Plant-damaging insects
*Plutella* test

| No. | Active compounds | Active compound concentration in ppm | Efficacy in % after 7$^d$ |
|---|---|---|---|
| 5 | [structure: 2,6-difluorophenyl-dihydropyrrole-phenyl-pyridine-O-propyl] | 100 | 100 |

TABLE E-continued
Plant-damaging insects
Plutella test
| No. | Active compounds | Active compound concentration in ppm | Efficacy in % after 7ᵈ |
|---|---|---|---|
| 4 | 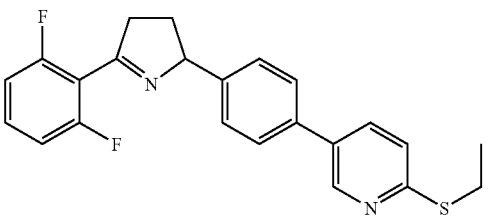 | 100 | 100 |
| 8 | 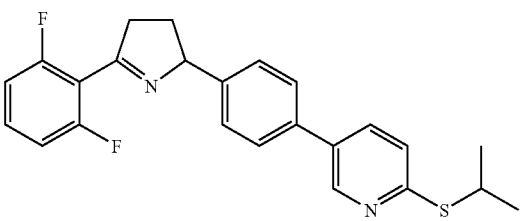 | 100 | 100 |
| 7 | 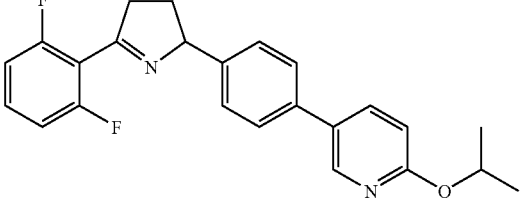 | 100 | 100 |
| 15 | 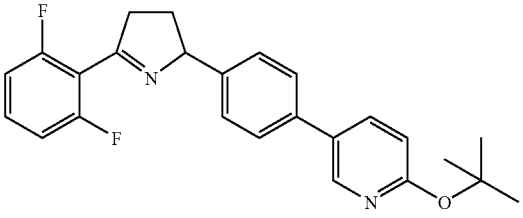 | 20 | 100 |
| 25 | 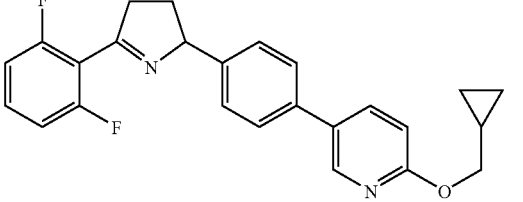 | 20 | 100 |

Example F

| Spodoptera exigua test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera exigua*) caterpillars whilst the leaves are still moist.

After the desired period of time, the kill in % is determined. 100% means that all caterpillars have been killed; 0% means that none of the caterpillars has been killed.

In this test, for example, the following compounds from the preparation examples display good activity:

TABLE F

Plant-damaging insects
*Spodoptera exigua* larvae test

| No. | Active compounds | Active compound concentration in ppm | Efficacy in % after 7$^d$ |
|---|---|---|---|
| 5 | 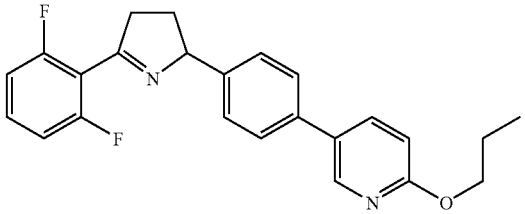 | 100 | 100 |
| 4 | 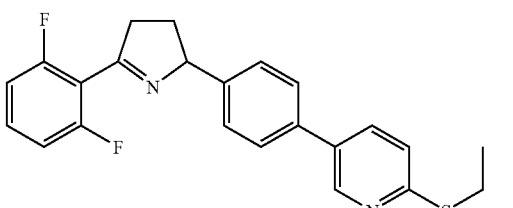 | 100 | 100 |
| 8 | 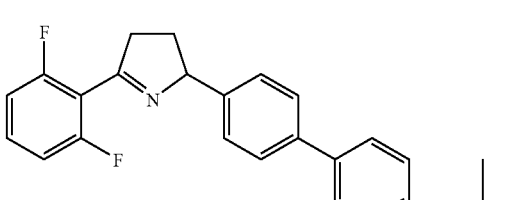 | 100 | 100 |
| 7 | 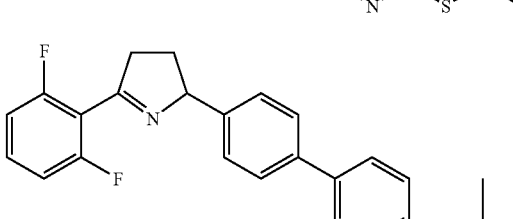 | 100 | 100 |
| 15 | 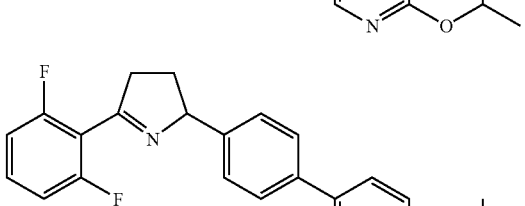 | 20 | 100 |

TABLE F-continued

Plant-damaging insects
*Spodoptera exigua* larvae test

| No. | Active compounds | Active compound concentration in ppm | Efficacy in % after 7$^d$ |
|---|---|---|---|
| 25 | 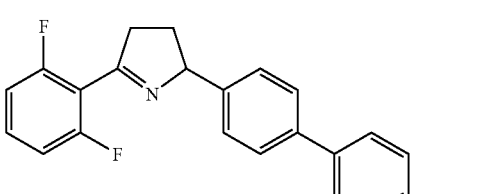 | 20 | 100 |

Example G

*Spodoptera frugiperda* test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with army worm (*Spodoptera frugiperda*) caterpillars whilst the leaves are still moist.

After the desired period of time, the kill in % is determined. 100% means that all caterpillars have been killed; 0% means that none of the caterpillars has been killed.

In this test, for example, the following compounds from the preparation examples display good activity:

TABLE G

Plant-damaging insects
*Spodoptera frugiperda* test

| No. | Active compounds | Active compound concentration in ppm | Efficacy in % after 7$^d$ |
|---|---|---|---|
| 1 | 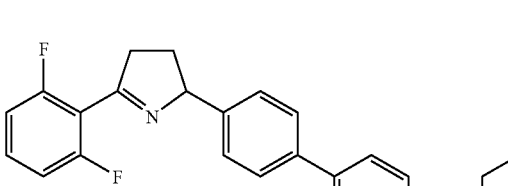 | 100 | 100 |
| 5 | | 100 | 100 |

TABLE G-continued

Plant-damaging insects
*Spodoptera frugiperda* test

| No. | Active compounds | Active compound concentration in ppm | Efficacy in % after 7$^d$ |
|---|---|---|---|
| 4 | [structure: 2,6-difluorophenyl-dihydropyrrole-phenyl-pyridine-S-ethyl] | 100 | 100 |
| 8 | [structure: 2,6-difluorophenyl-dihydropyrrole-phenyl-pyridine-S-isopropyl] | 100 | 100 |
| 7 | [structure: 2,6-difluorophenyl-dihydropyrrole-phenyl-pyridine-O-isopropyl] | 100 | 100 |
| 15 | [structure: 2,6-difluorophenyl-dihydropyrrole-phenyl-pyridine-O-tert-butyl] | 100 | 100 |
| 21 | [structure: 2,6-difluorophenyl-dihydropyrrole-phenyl-pyridine-O-cyclopentyl] | 100 | 100 |
| 25 | [structure: 2,6-difluorophenyl-dihydropyrrole-phenyl-pyridine-O-CH2-cyclopropyl] | 100 | 100 |

TABLE G-continued

Plant-damaging insects
*Spodoptera frugiperda* test

| No. | Active compounds | Active compound concentration in ppm | Efficacy in % after 7$^d$ |
|---|---|---|---|
| 19 | 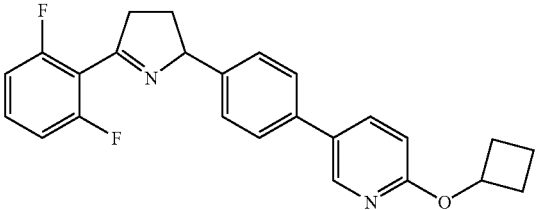 | 100 | 100 |

Example H

| *Tetranychus* test (OP resistant/dip treatment) | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites has been killed.

In this test, for example, the following compounds from the preparation examples display good activity:

TABLE H

Plant-damaging mites
Tetranychus-Test (OP-resistant/dip treatment)

| No. | Active compounds | Active compound concentration in ppm | Efficacy in % after 7$^d$ |
|---|---|---|---|
| 5 | 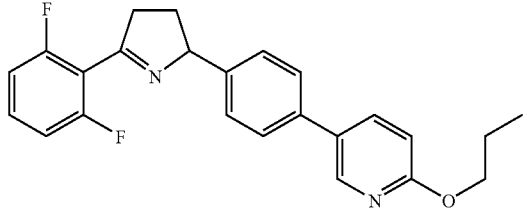 | 100 | 98 |
| 4 | 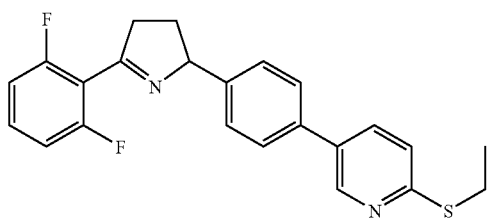 | 100 | 95 |

TABLE H-continued

Plant-damaging mites
Tetranychus-Test (OP-resistant/dip treatment)

| No. | Active compounds | Active compound concentration in ppm | Efficacy in % after 7$^d$ |
|---|---|---|---|
| 8 | [structure: 2,6-difluorophenyl-pyrroline-phenyl-pyridine-S-isopropyl] | 100 | 98 |
| 21 | [structure: 2,6-difluorophenyl-pyrroline-phenyl-pyridine-O-cyclopentyl] | 100 | 95 |
| 15 | [structure: 2,6-difluorophenyl-pyrroline-phenyl-pyridine-O-CH$_2$-cyclopropyl] | 100 | 95 |
| 19 | [structure: 2,6-difluorophenyl-pyrroline-phenyl-pyridine-O-cyclobutyl] | 100 | 95 |

Example I

*Panonychus* test

| | |
|---|---|
| Solvent: | 3 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Plum trees (*Prunus domestica*) about 30 cm high which are heavily infested by all stages of the fruit tree red spider mite (*Panonychus ulmi*) are dipped into a preparation of active compound of the desired concentration.

After the desired period of time, the effect in % is determined. 100% means that all spider mites have been killed; 0% means that none of the spider mites has been killed.

In this test, for example, the following compounds from the preparation examples display good activity:

TABLE I

Plant-damaging mites
*Panonychus* test

| No. | Active compound | Active compound concentration in ppm | Efficacy in % after 7$^d$ |
|---|---|---|---|
| 7 | (structure shown) | 100 | 100 |

Example K

Diabrotica balteata test (larvae in soil)
Critical concentration test/soil insects - treatment of transgenic plants

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example L

*Heliothis* virescens test (treatment of transgenic plants)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp. USA) are treated by being dipped into the preparation of active compound of the desired concentration and populated with the tobacco budworm caterpillar *Heliothis virescens* whilst the leaves are still moist.

After the desired period of time, the kill in % is determined. 100% means that all caterpillars have been killed; 0% means that none of the caterpillars has been killed.

Example M

Blowfly larvae test/development-inhibiting effect

| Test organisms: | *Lucilia cuprina* larvae |
|---|---|
| Solvent: | Dimethyl sulphoxide |

20 mg of active compound are dissolved in 1 ml of dimethyl sulphoxide; lower concentrations are prepared by dilution with distilled water.

About 20 Lucilia cuprina larvae are introduced into a test tube containing about 1 cm$^3$ of horse meat and 0.5 ml of the test preparation of active compound. After 24 and 48 hours, the activity of the preparation is determined. The test tubes are transferred to beakers with their bases covered with sand. After a further 14 days, the test tubes are removed and the pupae/flies are counted.

The effect of the preparation is assessed according to the number of flies which have hatched after 1.5 times the development period of an untreated control. 100% means that no flies have hatched; 0% means that all of the flies have hatched normally.

In this test, for example, the following compounds from the preparation examples display good activity:

TABLE M

| | Blowfly larvae test/development-inhibiting action | | |
|---|---|---|---|
| No. | Active compound | Active compound concentration in ppm | % Activity/ kill (48 h) |
| 25 | 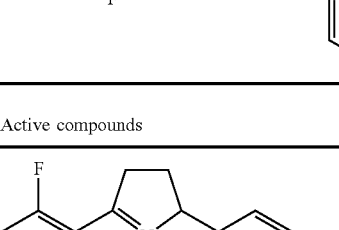 | 100 | 100 |

| No. | Active compounds | Active compound concentration in ppm | % Activity/ kill (14 d) |
|---|---|---|---|
| 25 | 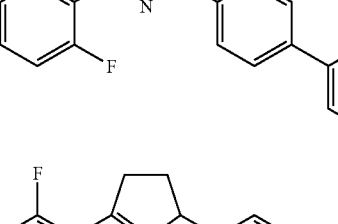 | 20 | 100 |
| 19 | 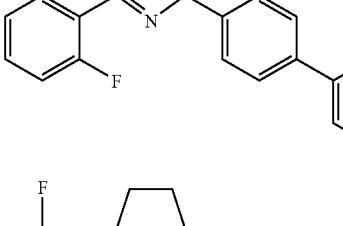 | 100/20 | 100/100 |
| 4 | 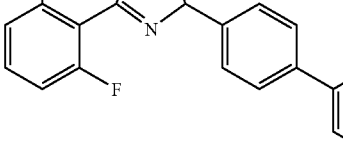 | 100 | 100 |

What is claimed is:

1. A $\Delta^1$-pyrroline of formula (I)

(I)

in which
$R^1$ is halogen or methyl,
$R^2$ is hydrogen or halogen,
Y is O or S, and
$R^3$ is $C_1$–$C_4$-alkyl, $C_3$–$C_6$-cycloalkyl, or $C_3$–$C_6$-cycloalkyl-$C_1$–$C_2$-alkyl.

2. A $\Delta^1$-pyrroline of formula (I) according to claim 1 in which
$R^1$ is fluorine, chlorine, or methyl,
$R^2$ is hydrogen, fluorine, or chlorine,
Y is O or S, and
$R^3$ is $C_1$–$C_4$-alkyl, $C_3$–$C_6$-cycloalkyl, or $C_3$–$C_6$-cycloalkyl-$C_1$–$C_2$-alkyl.

3. A $\Delta^1$-pyrroline of formula (I) according to claim 1 in which
$R^1$ is fluorine or chlorine,
$R^2$ is hydrogen, fluorine, or chlorine,
Y is O or S, and
$R^3$ is methyl, ethyl, propyl, butyl, cyclopropyl, cyclobutyl, cyclopentyl, cyclohexyl, cyclopropyl-$C_1$–$C_2$-alkyl, cyclobutyl-$C_1$–$C_2$-alkyl, cyclopentyl-$C_1$–$C_2$-alkyl, or cyclohexyl-$C_1$–$C_2$-alkyl.

4. A $\Delta^1$-pyrroline of formula (I) according to claim 1 in which
$R^1$ is fluorine or chlorine,
$R^2$ is hydrogen or fluorine,
Y is O or S, and $R^3$ is methyl, ethyl, n-propyl, iso-propyl, n-butyl, iso-butyl, sec-butyl, tert-butyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, or cyclohexylethyl.

5. A $\Delta^1$-pyrroline of formula (I) according to claim 1 in which $R^1$ and $R^2$ are fluorine.

6. A $\Delta^1$-pyrroline of formula (I) according to claim 1 in which Y is oxygen.

7. A $\Delta^1$-pyrroline of formula (I) according to claim 1 in which Y is sulphur.

8. A $\Delta^1$-pyrroline of formula (I) according to claim 1 in which $R^3$ is $C_1$–$C_4$-alkyl.

9. An (R)-configured compound of formula (I-a)

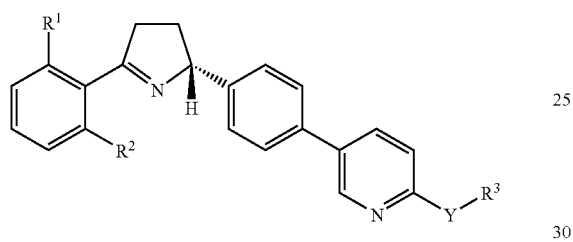

(I-a)

in which $R^1$, $R^2$, and $R^3$ as defined for formula (I) in claim 1.

10. A process for preparing a compound of formula (I) according to claim 1 comprising (A) reacting, in a tandem reaction, a $\Delta^1$-pyrroline of formula (II)

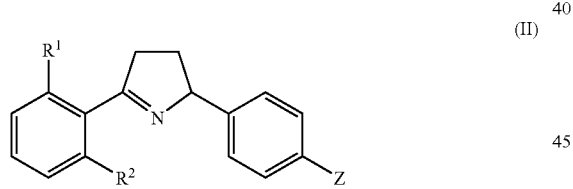

(II)

in which $R^1$ and $R^2$ are as defined for formula (I) in claim 1, and

Z is chlorine, bromine, iodine, —OSO$_2$CF$_3$, or —OSO$_2$(CF$_2$)$_3$CF$_3$, with a heterocycle of formula (III)

(III)

in which

Y and $R^3$ are as defined for formula (I) in claim 1, and

X is chlorine, bromine, iodine, —OSO$_2$CF$_3$ or —OSO$_2$(CF$_2$)$_3$CF$_3$, in the presence of a catalyst, in the presence of a diboronic ester, optionally in the presence of an acid binder, and optionally in the presence of a diluent, or (B) reacting a $\Delta^1$-pyrroline of formula (IV)

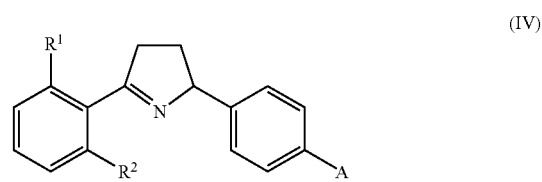

(IV)

in which $R^1$ and $R^2$ are as defined for formula (I) in claim 1, and

A is —B(OH)$_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, with a heterocycle of formula (III)

(III)

in which

Y and $R^3$ are as defined for formula (I) in claim 1, and

X is chlorine, bromine, iodine, —OSO$_2$CF$_3$ or —OSO$_2$(CF$_2$)$_3$CF$_3$, in the presence of a catalyst, optionally in the presence of an acid binder, and optionally in the presence of a diluent, or (C) reacting a $\Delta^1$-pyrroline of formula (II)

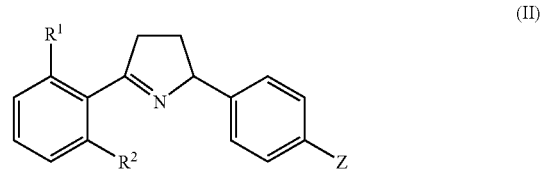

(II)

in which $R^1$ and $R^2$ are as defined for formula (I) in claim 1, and

Z is chlorine, bromine, iodine, —OSO$_2$CF$_3$, or —OSO$_2$(CF$_2$)$_3$CF$_3$, with a boronic acid derivative of formula (V)

(V)

in which

Y and $R^3$ are as defined for formula (I) in claim 1, and

A is —$B(OH)_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, in the presence of a catalyst, optionally in the presence of an acid binder, and optionally in the presence of a diluent, or (D) reacting a $\Delta^1$-pyrroline of formula (II-a)

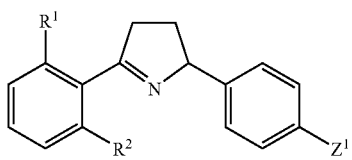

(II-a)

in which $R^1$ and $R^2$ are as defined for formula (I) in claim 1, and $Z^1$ is bromine or iodine, with an organometallic compound of formula (VI)

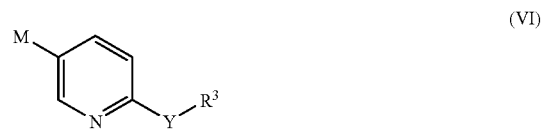

(VI)

in which

Y and $R^3$ are as defined for formula (I) in claim 1, and

M is ZnCl, $Sn(Me)_3$, or $Sn(n-Bu)_3$, in the presence of a catalyst, optionally in the presence of an acid binder, and optionally in the presence of a diluent.

11. A pesticide comprising one or more compounds of formula (I) according to claim 1 and one or more extenders and/or surface-active substances.

12. A method of controlling pests comprising causing an effective amount of one or more compounds of formula (I) according to claim 1 to act on pests and/or their habitat.

13. A process for preparing pesticides comprising mixing one or more compounds of formula (I) according to claim 1 with one or more extenders and/or surface-active substances.

* * * * *